United States Patent [19]

White et al.

[11] Patent Number: 5,347,046
[45] Date of Patent: Sep. 13, 1994

[54] CATALYST AND PROCESS FOR USING SAME FOR THE PREPARATION OF UNSATURATED CARBOXYLIC ACID ESTERS

[75] Inventors: James F. White, Hudson; Barbara Slawski, Parma; Geoffrey White, Shaker Heights, all of Ohio

[73] Assignee: Engelhard Corporation, Iselin, N.J.

[21] Appl. No.: 67,445

[22] Filed: May 25, 1993

[51] Int. Cl.$^5$ .................. C07C 67/05; B01J 31/00; B01J 23/58
[52] U.S. Cl. ................................................ 560/245
[58] Field of Search ............................. 560/245, 243

[56] References Cited

U.S. PATENT DOCUMENTS

| | | | |
|---|---|---|---|
| 3,346,624 | 10/1967 | Schaeffer et al. | 260/497 |
| 3,346,626 | 10/1967 | Schaeffer et al. | 260/497 |
| 3,373,189 | 3/1968 | Lum | 260/497 |
| 3,471,532 | 10/1969 | Young | 260/410.9 |
| 3,557,192 | 1/1971 | Hillman | 260/497 |
| 3,579,569 | 5/1971 | Montgomery et al. | 260/497 |
| 3,622,620 | 11/1971 | Horiie | 260/497 |
| 3,650,986 | 3/1972 | Sennewald et al. | 252/431 |
| 3,655,747 | 4/1972 | Sennewald et al. | 260/530 |
| 3,743,607 | 7/1973 | Sennewald et al. | 252/430 |
| 3,758,551 | 9/1973 | Murib et al. | 560/208 |
| 3,761,513 | 9/1973 | Sennenwald et al. | 560/245 |
| 3,775,342 | 11/1973 | Kronig et al. | 252/430 |
| 3,822,308 | 7/1974 | Kronig et al. | 260/497 |
| 3,939,199 | 2/1976 | Fernhotz et al. | 260/469 |
| 3,946,068 | 3/1976 | Calcagno et al. | 260/497 |
| 3,970,697 | 7/1976 | Scheben et al. | 562/548 |
| 4,048,096 | 9/1977 | Bissot | 252/430 |
| 4,057,575 | 11/1977 | Klass | 560/245 |
| 4,119,567 | 10/1978 | Bartsch | 252/430 |
| 4,133,962 | 1/1979 | Fernholz et al. | 560/245 |
| 4,490,481 | 12/1984 | Boitiaux et al. | 502/330 |
| 4,533,779 | 8/1985 | Boitiaux et al. | 585/259 |
| 4,902,823 | 2/1990 | Wunder et al. | 560/245 |
| 5,194,417 | 3/1993 | Smith et al. | 502/330 |

FOREIGN PATENT DOCUMENTS

| | | |
|---|---|---|
| 948211 | 5/1974 | Canada . |
| 2601154 | 7/1977 | Fed. Rep. of Germany . |
| 681437 | 5/1979 | South Africa . |
| 682015 | 6/1979 | South Africa . |
| 695822 | 8/1979 | South Africa . |
| 976613 | 3/1963 | United Kingdom . |
| 1116588 | 12/1966 | United Kingdom . |
| 1067850 | 5/1967 | United Kingdom . |
| 1154517 | 6/1967 | United Kingdom . |
| 1086347 | 10/1967 | United Kingdom . |
| 1216499 | 12/1967 | United Kingdom . |
| 1216500 | 12/1967 | United Kingdom . |
| 1209125 | 3/1969 | United Kingdom . |
| 1283737 | 8/1969 | United Kingdom . |
| 1571910 | 12/1976 | United Kingdom . |
| 1521652 | 1/1977 | United Kingdom . |
| 1511869 | 5/1978 | United Kingdom . |
| 1559540 | 1/1980 | United Kingdom . |

OTHER PUBLICATIONS

"Selectivity Problems & Kinetic Models in the Palladium Catalysed Oxidation of Ethyene & Acetic Acid to (List continued on next page.)

*Primary Examiner*—Arthur C. Prescott

[57] ABSTRACT

Disclosed are catalyst compositions comprising (i) one or more palladium group metals and/or compounds thereof; (ii) gold and/or compounds thereof; and (iii) optionally, an effective amount of one or more promoters selected from the group consisting of copper, nickel, cobalt, iron, manganese, lead, silver and compounds thereof. Preferably these catalyst compositions contain one or more promoters wherein the gram ratio of metal in the promoter to palladium group metal is up to about 0.4, wherein the catalysts are deposited on a support material and said support material is treated with one or more alkali metal bases and one or more alkali metal silicates prior to said deposition.

Also described are processes for preparing ethylenically unsaturated esters comprising reacting in the vapor phase at least one olefinic compound with at least one carboxylic organic acid and molecular oxygen in the presence of an effective amount of the foregoing catalyst compositions.

17 Claims, No Drawings

OTHER PUBLICATIONS

Ethenyl Acetate Related Reactions of Propene, 1-Butene and 1-Hexene", Davidson, Mitchell, Raghavan, Proceedings of the International Chemical Reaction Conference, p. 300 (1989).

"Manufacture of Vinyl Acetate from Ethylene" by R. Shelty & Chandalia, Chem. Proc. & Eng., (Sep. 1969).

"The Mechanism of Vinyl Acetate Formation by Gas–-Phase Catalytic Ethylene Acetoxidation", Samanos, Boutry, Montaranal, Journal of Catalysis 23, 19–30 (1971).

Wacker Oxidation Catalysis In a Supported Aqueous Phase Carhancet Davis Hanson, Sep. 91, Catalysis Letters 129–136.

"Catalytic Activity of Supported Liquid Phase Lithium-Palladium Acetate Catalysts in the Oxidation of Ethylene to Vinyl Acetate", Zaidi, Applied Catalysis (1988) 353–358.

Vinyl Polymers, Kirk Othmer Encyclopedia of Chemical Technology, 3rd Ed., p. 817, J. Wiley & Sons (1983).

Chemistry of Catalytic Processes; Gates, Katzer, G. C. A. Schvit p. 137, McGraw-Hill (1979).

"Ethylene And Its Derivatives", ED by S. A. Miller, Chapter 12, p. 942 (1974).

"Mechanism of Palladium–Catalyzed Synthesis of Vinyl Acetate from Ethylene in a Heterogenous Gas Reaction", Nakamura, Yasui; Journal of Catalysis, 17, 366–374 (1970).

Production of Vinyl Acetate by Acetoxidation of Ethyleen, Shelty, Kashyap, Chandalia, Indian Journal of Technology, vol. 11, 1973, pp. 170–173.

Make Vinyl Acetate Via Ethylene, Schwerdtel, Hydrocarbon Processng, p. 187, vol. 47 #11, (1968).

Vinyl Acetate: how, where, who–future, Stobaugh, Allen, Sternberg, Hydrocarbon Processing, Petrochemical Guide, Part 18, pp. 153–161 May 1992.

CATALYST AND PROCESS FOR USING SAME FOR THE PREPARATION OF UNSATURATED CARBOXYLIC ACID ESTERS

BACKGROUND OF THE INVENTION

1. Field of the Invention

This invention relates to novel catalysts useful in the preparation of unsaturated organic esters from olefinic compounds, oxygen, and carboxylic acids and to processes for using these catalysts.

2. Description of Related Art

A number of processes for preparing unsaturated organic esters are well known to those in art. The predominant industrial use of such processes is for the preparation of vinyl acetate. Processes for preparing vinyl acetate include, for example, U.S. Pat. No. 3,346,624 which describes a liquid phase process for the oxidation of ethylene to vinyl acetate and acetaldehyde by contacting ethylene with oxygen in a reaction medium comprising a carboxylic acid in the presence of a platinum group metal salt and a redox agent such as chlorides of copper. The redox agent functions as an oxidant to keep palladium in the oxidized state and prevent the palladium from precipitating out of solution and thus becoming inactive for the process.

British patent 976,613 describes the reaction of an unsaturated organic compound, a carboxylic organic acid, oxygen or an oxygen containing gas in the gas phase in the presence of a group VIII noble metal catalyst to form the corresponding ester. The catalyst may be unsupported or supported on a material such as carbon, silica or alumina and may contain 1:10 equivalent per equivalent of catalyst of a metal halide promoter such as cooper chloride.

British patent 1,521,652 describes a catalyst for making vinyl acetate in the gaseous phase from ethylene, oxygen and acetic acid. This patent describes catalysts in the form of particles, each particle comprising a mixture of palladium and gold as noble metals and a support material and having (a) an outer layer of low or zero noble metal content, (b) an inner shell rich in noble metal and (c) a core having low or zero noble metal content.

U.S. Pat. No. 4,048,096 describes a palladium-gold catalyst for the production of vinyl esters such as vinyl acetate by the vapor phase reaction of ethylene, oxygen and a carboxylic acid. Described is a catalyst prepared by impregnating a catalyst support with aqueous solution of water soluble palladium and gold compounds, precipitating water insoluble palladium and gold compounds onto the catalyst support by contacting the impregnated catalyst support with a solution of compounds capable of reacting with the water soluble palladium and gold compounds to form water insoluble palladium and gold compounds (e.g., sodium silicates), converting the water insoluble palladium and gold compounds into palladium and gold metal by treatment with a reducing agent, washing the catalyst with water, and contacting the catalyst with alkali metal acetate and drying the catalyst.

U.S. Pat. No. 4,119,567 describes a supported catalyst composition for the preparation of unsaturated organic esters by the vapor phase reaction of an olefinic compound, oxygen and a lower carboxylic acid; the catalyst containing a Group VIII noble metal. Described is an alumina carrier having an alumina content greater than 99%, a crystalline alpha-alumina content of greater than 96%, a theta-alumina content of less than about 3%, a total calcium and magnesium content of less than 750 ppm, a surface area of about 2 to 6m$^2$/g, an average crush strength of from about 20 to 45 lbs., a bulk density of less than about 1.35 g/cc, and an acetic acid loading of less than about 1.5% in 200 hrs. The catalyst is also described as generally containing an alkali metal carboxylate activator and optionally a metal such as gold and copper.

U.S. Pat. No. 3,743,607 describes a catalyst for the catalytic, vapor phase production of vinyl acetate from ethylene, acetic acid and molecular oxygen. Described is a catalyst comprised of palladium and an alkyl metal acetate or formate supported on a carrier and is activated by including metallic gold therein.

There is still a need, however, for catalysts and processes for the production of unsaturated organic esters such as vinyl acetate which provide improved activity and selectivity.

SUMMARY OF THE INVENTION

This invention relates to catalysts and processes for the preparation of ethylenically unsaturated organic esters.

In one embodiment, this invention relates to a composition suitable for use as a catalyst for the preparation of ethylenically unsaturated organic esters in the vapor phase from olefinic compounds, oxygen and carboxylic acids comprising (i) one or more palladium group metals and/or compounds thereof, (ii) gold and/or compounds thereof and (iii) an effective amount of one or more promoters selected from the group consisting of copper, nickel, cobalt, iron, manganese, lead, silver and compounds thereof, wherein the gram-atom ratio of metal in the promoter to palladium group metal is up to about 0.4.

In a further embodiment, this invention relates to a composition suitable for use as a catalyst in the preparation of ethylenically unsaturated organic esters in the vapor phase from olefinic compounds, oxygen, and carboxylic aids comprising (i) one or more palladium group metals and/or compounds thereof; (ii) gold and/or compounds thereof; and (iii), optionally, an effective amount of one or more promoters selected from the group consisting of copper, nickel, cobalt, iron, manganese, lead, silver and compounds thereof; wherein (i), (ii) and, optionally, (iii) are deposited on a support material and said support material is treated with one or more alkali metal bases and one or more alkali metal silicates prior to said deposition.

In another embodiment, this invention relates to a process for preparing ethylenically unsaturated esters comprising reacting in the vapor phase at least one olefinic compound with at least one carboxylic organic acid and molecular oxygen in the presence of an effective amount of a catalyst composition comprising (i) one or more palladium group metals and/or compounds thereof, (ii) gold and/or compounds thereof and (iii) an effective amount of one or more promoters selected from the group consisting of copper, nickel, cobalt, iron, manganese, lead, silver and compounds thereof, wherein the gram-atom ratio of metal in the promoter to palladium group metal is up to about 0.4.

In a still further embodiment, this invention relates to a process for preparing ethylenically unsaturated esters comprising reacting in the vapor phase at least one olefinic compound with at least one carboxylic acid and molecular oxygen in the presence of an effective amount of a catalyst composition comprising (i) one or more palladium group metals and/or compounds thereof; (ii) gold and/or compounds thereof; and (iii), optionally, an effective amount of one or more promoters selected from the group consisting of copper, nickel, cobalt, iron, manganese, lead, silver and compounds thereof; wherein said catalyst is deposited on a support material and said support material is treated with one or more alkali metal bases and one or more alkali metal silicates prior to said deposition.

DESCRIPTION OF THE PREFERRED EMBODIMENT

As previously stated this invention provides catalysts and processes for the preparation of ethylenically unsaturated esters by the vapor phase reaction of one or more olefinic compounds, molecular oxygen and one or more carboxylic acids. The catalysts of this invention contain palladium group metals and/or compounds thereof. As used herein, "palladium group metals" shall mean noble metals selected from the group consisting of palladium, ruthenium, rhodium, osmium, iridium and platinum. The palladium group metal is preferably in the metal form, but can also be a compound thereof such as an oxide or salt thereof, either organic or inorganic. Specific examples of which include palladium, rhodium, platinum, ruthenium, osmium, iridium, palladous benzoate, palladous acetate, palladous propionate, ruthenium acetate, platinous benzoate, rhodium acetate, palladous chloride, palladous oxide, palladous bromide, palladous sulfate, platinum disulfide, platinum oxide, rhodium chloride, rhodium trichloride, rhodium oxide, ruthenium chloride, ruthenium oxide, iridium oxide and mixtures thereof.

Catalysts of this invention also contain gold in the metal formand/or compounds thereof which include oxides, halides, sulfates, nitrites, acetates, etc. Suitable gold compounds include gold chloride, $AuCl_3$, tetrachloroauric (III) acid $(H[AuCl_4].4H_2O)$ and sodium gold tetrachloride $(Na[AuCl_4].4H_2O)$.

In a preferred embodiment, the catalysts of this invention also contain one or more promoters selected from the group consisting of copper, nickel, cobalt, iron, manganese, lead, silver and compounds thereof. These promoters may be in the form of metals or compounds thereof, either organic or inorganic, including oxides, hydroxides and salts, such as acetates, chloroacetates, carbonates, bicarbonates and cyanides thereof. Particularly preferred are copper, nickel, cobalt and silver.

When the promoter is present in the catalyst, it is in an amount which is sufficient to be effective in promoting the catalytic reaction of one or more olefinic compounds, molecular oxygen and one or more carboxylic acids to form ethylenically unsaturated organic esters. Typically, the gramatom ratio of metal in the promoter to palladium group metal does not exceed about 0.4; preferably is at least about 0.04 and more preferably is from about 0.1 up to about 0.2.

The catalysts of this invention shall typically have a gram-atom ratio of gold to palladium group metal of from about 0.1 up to about 0.5, preferably from about 0.2 up to about 0.3.

The catalysts of this invention may be unsupported or supported on a suitable material. The catalysts are usually in a form suitable for use in a fixed bed reactor or a fluid bed application. Typically, the catalyst of this invention is supported. The support suitable for use in this invention is an inert carrier such as alumina, silica, silica-alumina, silicic acid, titania, carbon or mixtures of barium, strontium or calcium carbonates with silica and/or alumina.

The carrier may be of any configuration, shape or size which exposes the catalyst supported thereon to the reactants being catalyzed. For example, the carrier may be a powder or formed into shapes such as tablets, pellets, spheres, cylinders, irregular granules, rings, stars, etc. The total porosity of such carrier as measured by the absorption of liquid water at room temperature and under atmospheric pressure is typically in the range of from about 0.1 up to about 1.5 cc of water per gram of support and preferably from about 0.25 cc per gram up to about 0.45 cc per gram and more preferably from about 0.45 cc per gram up to about 0.85 cc per gram.

In a preferred embodiment, the support material is pre-treated with one or more alkali or alkaline earth met-al bases and one or more alkali and/or alkaline earth metal silicates. The amount of alkali or alkaline earth base used in the pretreatment of the support is typically from about 0.02 mole up to about 1.25 moles per liter of support. Preferably the amount of such base is from about 0.15 mole up to about 0.8 mole per liter of support and most preferably is 0.2 mole up to about 0.4 mole of such base per liter of support.

The amount of alkali or alkaline earth silicate used in the pretreatment of the support, calculated as silicon dioxide and expressed as an amount which is a percent by weight of the support, is typically from about 0.15% up to about 15%; preferably it is 1% up to about 10% and more preferably from about 2.5% up to about 7%.

The base and silicate may be applied sequentially or simultaneously by means known in the art. The pretreatment can be accomplished by such conventional treatments as spraying, washing, immersion, etc. The preferred method is to spray the support with an aqueous or alcoholic solution of the pre-treatment agents. As previously mentioned, the base and the silicate may be applied to the support separately and drying between applications is optional. It is preferred, however, that the pre-treated support be dried prior to deposition of the catalysts of this invention. After pretreatment but before drying, the pretreated support may be aged by holding it for up to 100 hours or more at ambient conditions; preferably, from about 16 to about 48 hours at room temperature in a closed vessel at atmospheric pressure. Following the treatment of the carrier with the base and silicate solution, the carrier is dried to lower the water or alcohol content. As used herein the pretreated carrier is typically considered dry when the residual moisture (alcohol or water) content of the support is less than about 35%, preferably less than about 15% and more preferably less than about 7%. Conventional drying procedures may be employed here, although a warm, inert gaseous stream is preferably passed over or through the carrier. The gases used for this purpose include air, nitrogen, argon, and the like as well as mixtures thereof. The temperature of the gaseous stream is not critical and may vary from about 40° to about 150° C., but preferably from about 50° up to about 100° C.

The alkali and alkaline earth metal bases and silicates can be derived from any alkali or alkaline earth metals, however for cost and availability reasons, the sodium and potassium salts are preferred. The preferred bases are alkali metal bases such as sodium hydroxide, sodium carbonate, sodium bicarbonate, disodium hydrogen phosphate, potassium carbonate, potassium hydroxide and the like or mixtures thereof. The silicates can vary from sodium orthosilicate ($Na_4SiO_4$), through sodium metasilicate ($Na_2SiO_3$), sodium disilicate ($Na_2Si_2O_5$) to commercial alkali silicate or water glass solutions of indefinite compositions ($M_2O.XSiO_2$) where M is one or more alkali metals and X is from about 1.6 to about 5. The preferred source of silicates are the commercial alkali silicate solutions such as those supplied by PQ Corporation, Valley Forge, PA and designated as N, O, E, Kasil, etc.

The palladium group metals, gold, and promoters can be dispersed onto the support by means that are known in the art such as co-precipitation or impregnation. They can all be impregnated simultaneously or sequentially in any order. Impregnation is the preferred method. Impregnation may be carried out by techniques well known to those of ordinary skill in the art.

For example, the carrier may be impregnated with a solution containing compounds of the desired metals. The solution may be an aqueous solution, one using organic solvents or a mixture of the two, with an aqueous solution being preferred.

The impregnation of a carrier can be accomplished by spraying the carrier with a solution of the metal compound or admixtures thereof. Metal compounds include salts such as halides, sulfates, nitrates, acetates, etc. When mixtures of metals are to be simultaneously deposited, the salts of the metals are preferably the same, although this is not critical. The preferred anions are chlorides, bromides and nitrates, and the use of chlorides is especially preferred. Aqueous solutions are preferred, although other solvents can be employed. In general, the concentration of the metal salts in the aqueous solution will range from about 1% to 50%, preferably from about 2% to 25% by weight based on the total weight of the solution. The pH of the solution may vary from about 0.5 to about 6.5. When two or more metals are to be deposited, they may be present in varying amounts and deposited simultaneously or sequentially. This step is generally carried out under ambient conditions of temperature and pressure, though these operating conditions are not critical.

After the palladium group metals, gold and promoter metals have been placed on the carrier support, they are usually subject to reduction treatment to convert metal oxides or hydroxides to catalytically active metals. Conventional reduction procedures and agents such as hydrogen, carbon monoxide, diborane and the like may be utilized. Thermal decomposition of the metal salts as well as direct reduction in aqueous and non-aqueous suspension by such materials as aqueous formic acid, aqueous salts of formic acid, aqueous solutions of formaldehyde, aqueous alkaline formaldehyde, aqueous hydrazine, aqueous or alcoholic sodium borohydride, triethylaluminum, etc., can also be employed. Use of molecular hydrogen at temperatures ranging from 50° to 250° C. is especially preferred because of simplicity. The amount of reducing agent required is preferably only enough to reduce all of the metals on the carrier to their elemental state, although amounts in excess of the requisite stoichiometric amount of reducing agent may be used.

In some instances, it has been found advantageous to wash or reduce the catalyst particles with deionized water one or more times to remove excess base or by-products formed by reduction of the metal salts. If this is employed, the catalyst is finally dried at temperatures of from 80° to 150° C. under in an inert atmosphere or under reduced pressure.

The catalysts of this invention may also contain one or more alkali or alkaline earth salts of an organic acid such as lithium, sodium, calcium or potassium acetate as a promoter and activator. These organic acid salts may be added to the catalyst in amounts up to 50 grams per liter of catalyst and preferably in the range of 15 to 35 grams per liter of catalyst.

The above-described catalysts can be used in the vapor phase preparation of ethylenically unsaturated esters from olefinic compounds, oxygen and carboxylic acids.

The olefinic compounds used in accordance with this invention may be any olefinic or diolefinic hydrocarbon. Suitable olefinic hydrocarbons are ethylene, propylene, alphabutylene, beta-butylene, pentene, and its homologs, cyclohexene, and styrene. Mixtures of olefins or gases containing olefins or other unsaturated compounds may be used in the reaction of this invention provided they are capable of reacting under the reaction conditions. Olefins containing two or three carbon atoms constitutes a preferred group of starting materials. Under certain reaction conditions it may be necessary to adjust temperature and pressure so that the reaction will go forward with the particular olefins taking into account their physical properties. Where higher olefins are used, the products will have a correspondingly higher boiling point which may also require corresponding modifications in the reaction conditions. The unsaturated organic acids used in accordance with this invention have the formula $R'(COOH)_m$, wherein $R'$ is any hydrocarbon radical having one to twenty carbon atoms and m has the value of 1 to 5. Where $R'$ is an aliphatic radical the following acids are intended: acetic acid, propionic acid, n-butyric acid, isobutyric acid, n-valeric acid, trimethylacetic acid, caproic acid, n-heptylic acid, caprylic acid and perlargonic acid. Where $R'$ is an aromatic radical and alkylaryl radical, an aralkyl radical or the like, the following acids are contemplated: benzoic, o-toluic, m-toluic, p-toluic, salicylic, anisic, phthalic, terephthalic, hemimellitic, trimelitic, trimesic, prehnitic, phenylacetic, hydrocinnamic, gamma-phenyl- butyric, delta-phenyl-N-valeric, epsilon-phenyl-n-caproic, homophthalic, o-phenylenediacetic, m-phenylenediacetic, p-phenylenediacetic, o-phenyleneacetic-beta-propionic acid.

Alkali and alkaline earth metals salts of these acids in mixtures with the acids may also be used. Thus, the reaction can be carried out using sodium acetate, calcium acetate, potassium propionate, barium isobutrate, calcium acetate, magnesium acetate, magnesium butrate, sodium valerate, lithium trimethyl- acetate, barium caproate, and the like as part of the acid-producing ingredients.

Examples of $R'$ groups coming within the foregoing definition are methyl, ethyl, propyl, isopropyl, butyl, isobutyl, t-butyl, amyl, isoamyl, hexyl, isohexyl, heptyl, octyl, nonyl, decyl, undecyl, dodecyl, tridecyl, tetradecyl, pentadecyl, hexadecyl, heptadecyl, octadecyl, nonadecyl, and eicosyl groups. Other acids that can be used include isovaleric, methylethylacetic, isocaproic, methyl-n-propylacetic, diethylacetic, secbutylacetic, dimethylethylacetic, tert-butylacetic, methyl-isopropylacetic, methyl-t-butyneopentylacetic, myristic, palmitic, margaric, and dicetylacetic acid.

The preferred ethylenically unsaturated ester is vinyl acetate which in general is prepared by passing acetic acid, ethylene, and molecular oxygen or molecular oxygen-containing gases over the catalysts described herein at temperatures of 100° to 220° C., preferably 120° to 200° C. under pressures of 1 to 25 bar, preferably 2 to 15 bar.

The oxygen concentration is advantageously kept below 15% by volume (based on the total feed gas composition including carboxylic acid vapor in the mixture), preferably below 10% and more preferably below 8%. In any case, it is preferable to keep the oxygen composition of the gas such that it is below the explosive range so that the process can be conducted safely. Under certain circumstances, however, dilution with inert gases such as nitrogen or carbon dioxide, is also advantageous. $CO_2$ in particular is suitable for dilution in certain processes since it is formed in small amounts during the reaction. Within the limits shown above the oxygen concentration, the amounts of the other reactants such as acetic acid and ethylene may vary widely. It is desirables however, that the olefinic compound be kept in stoichiometric excess over the carboxylic acid such that the volume ratio of olefin to acid vapor in the feed mixture is from about 1.8 up to about 5.0 and preferably from about 3.0 to about 5.0.

Examples of this invention are included hereinbelow. Of course, these examples are not intended as limiting this invention as modification of the examples by ordinary expedient will be readily apparent to those of ordinary skill in the art.

Unless otherwise indicated in the following examples and elsewhere in the specification and claims, all parts and percentages are by weight, temperatures are in degrees centigrade and pressures are at or near atmospheric.

Unless otherwise noted, the following examples are prepared using a spherical silica bead known as KA-160 commercially available from Sud-Chemie which is nominally 5mm in diameter and is characterized by a water adsorption pore volume of from about 0.52 to about 0.67 cc per gram of bead, a bulk density in the range of about 565 to 590 grams per liter and the B.E.T. surface area is about 160 m² per gram.

EXAMPLE 1

Pretreated silica beads are prepared by impregnating 7½ liters, 4350 grams, of KA-160 with 2400 cc of an aqueous pretreatment solution containing 123.1 grams of potassium hydroxide and 954 grams of a potassium silicate solution commercially available as KASIL No. 6 from the PQ Corp. of Valley Forge, Pa. containing 26.5% by weight of silica. The beads are impregnated by uniformly spraying the pretreatment solution on the beads over a period of about 20 minutes while they are tumbled and mixed in a rotating plastic coater. On a per liter basis the support is pretreated with 16.2 grams of KOH and 127.2 grams of potassium silicate solution. The pretreated beads are aged in a closed vessel at room temperature for about 60 hours and then dried with a flowing air stream at about 70° C. in a vibrating laboratory drier to a residual moisture level of less than 2%. The resulting pretreated beads have a water adsorption porosity of 0.52 cc/gram and a bulk density of 667 grams per liter.

EXAMPLE 2

A Pd-Au-Cu catalyst is prepared by impregnating the pretreated beads of Example 1 with 137.8 cc of an aqueous solution containing 9.95 grams of sodium palladium tetrachloride solution (16.49% Pd), 3.26 grams of sodium gold tetrachloride solution (22.09% Au) and 0.32 grams of cupric chloride dihydrate. The impregnation is accomplished by uniformly spraying the pretreated beads with the Pd-Au-Cu solution while the beads are tumbled and mixed in a rotating coater.

The Pd-Au-Cu impregnated beads are aged in a closed container for about 44 hours at room temperature and then reduced in 250 cc of deionized water containing 6 grams of hydrazine, held in contact with the hydrazine solution for two hours, washed with flowing deionized water until the wash water has a conductivity of under 100 micro mhos, and then dried at 110°-120° C. to a residual moisture content of less than 2%. The catalyst obtained nominally contains 4.1 g of Pd, 1.8 g of Au and 6.3 g of Cu per liter of catalyst.

EXAMPLE 3

The catalyst of Example 2 (400 cc, 260 grams) is further impregnated with 132.6 cc of an aqueous solution containing 8.8 grams of potassium acetate dissolved in deionized water by uniformly spraying the acetate solution on the catalyst while it is tumbled in a rotary coater. The potassium acetate impregnated catalyst is dried overnight in a forced air oven held at 110° C. to a moisture content of less than 2%. The catalyst obtained has a nominal loading of potassium acetate of 22 grams per liter of catalyst.

EXAMPLE 4

Pretreated silica beads are prepared by impregnating 20.6 liters, 11361 grams, of KA-160 beads with 7150 cc of an aqueous pretreatment solution containing 2,260 grams of the potassium silicate solution identified in Example 1 and 333.7 grams of potassium hydroxide. The beads are impregnated by uniformly spraying the pretreatment solution on the beads over a period of 35 minutes while they are tumbled in a rotating plastic coater. On a per liter basis, the support is pretreated with 16.2 grams of KOH and 109.7 grams of potassium silicate solution. The pretreated beads are aged at room temperature for five days and then dried with a flowing air stream at 50° C. to 75° C. while being tumbled in the rotating plastic coater. The resulting pretreated beads have a bulk density of 627 grams per liter and a water adsorption pore volume of 0.5 cc per gram.

EXAMPLE 5

A Pd-Au catalyst is prepared by impregnating one liter of the pretreated beads of Example 4 with 314 cc of an aqueous solution containing 4.2 grams of palladium (as 24.33 grams of sodium palladium tetrachloride solution having a Pd concentration of 17.27%) and 1.84 grams of gold (as 14.81 grams of sodium gold tetrachloride having a gold concentration of 12.46%). The impregnation is accomplished by uniformly spraying the pretreated beads with the Pd-Au solution while they are tumbled and mixed in a rotating coater. The beads are aged over 48 hours at room temperature and then reduced in 450 cc of water containing 6 grams of hydrazine for about one hour, then washed and dried as in Example 2. The resulting catalyst is further impregnated with potassium acetate to a level of 30.5 grams per liter by uniformly spraying on the catalyst an aqueous solution of 30.5 grams of potassium acetate diluted in deionized water to a volume of 330 cc., then dried at 110° C. overnight.

EXAMPLE 6

A Pd-Au catalyst is prepared by repeating the procedure of Example 5, except Pd-Au impregnated beads are aged for 40 hours in a closed vessel, reduced in 450 cc of deionized water combined with 17 grams of 35% hydrazine solution for about two hours, the beads are washed with flowing deionized water until the wash water conductivity is below 100 micro mhos and then dried in a forced air oven at 110° C. for 16 hours. The catalyst is further impregnated with potassium acetate as in Example 5.

EXAMPLE 7

A Pd-Au-Cu catalyst is prepared by impregnating one liter, 575 grams, of KA-160 silica beads with 339 cc of an aqueous solution containing 4.2 grams of palladium (as 24.31 grams of $Na_2PdCl_4$ having a Pd concentration of 17.27%), 1.84 grams of gold (as 10.05 grams of $NaAuCl_4$ having an Au concentration of 18.31%) and 0.307 grams of copper (as 0.824 grams of $CuCl_2-2H_2O$). The impregnation is accomplished by uniformly spraying the beads with the Pd-Au-Cu containing solution while being tumbled and mixed in a two liter titanium coater. The Pd-Au-Cu impregnated beads are aged for two hours at room temperature, soaked in a 5% aqueous solution of sodium meta silicate for 16 hours, then 17 grams of 35% aqueous hydrazine is mixed with the silicate solution containing the beads and held for about two hours, and then washing with flowing deionized water until the conductivity of the wash water is below 100 micro-mhos. The resulting catalyst is dried in a forced air oven at 110° C., then spray impregnated with 30 grams of potassium acetate dissolved in 324 cc of deionized water and dried again to a moisture level of less than 2% in a forced air oven.

EXAMPLE 8

Pretreated silica beads are prepared by impregnating one liter, 575 grams, of KA-160 silica with 170 cc of deionized water containing 22 grams of potassium hydroxide by uniformly spraying the beads while they are tumbled and mixed in a rotating coater. The KOH treated beads are aged while tumbling in the rotating titanium coater for about 15 minutes then the following Pd-Au-Cu solution is uniformly sprayed onto the KOH treated beads while they are mixed and tumbled in a rotating coater: 0.3 grams of copper, as 0.804 grams of copper chloride dihydrate, 4.1 grams Pd, as 23.74 grams of sodium palladium tetrachloride solution having a Pd concentrate of 17.27% by weight, and 1.8 grams of gold, as 9.83 grams of sodium gold tetrachloride solution having a gold concentration of 18.31% by weight, diluted with deionized water to a volume of 170 cc.

These Pd-Au-Cu impregnated beads are aged at room temperature in a closed vessel for 16 hours, the catalyst is reduced, washed, and dried in the same way as for the above Example 7. The catalyst is further impregnated by spraying it with 30 grams of potassium acetate diluted in deionized water to 350 cc. The catalyst is then dried in a forced air oven at 110° C. overnight.

EXAMPLE 9

Pretreated silica beads are prepared by impregnating one liter, 566 grams, of KA-160 silica (dried overnight at 120° C.) with 362 cc of a solution containing 25.56 grams of potassium hydroxide using the spray coating technique described in Example 1. The pretreated beads are then aged and dried in the same way as Example 1. The pretreated beads are then impregnated with 328 cc of a solution containing 4.1 grams of Pd, as 23.74 grams of $Na_2PdCl_4$ having a Pd concentration of 17.27%, 1.8 grams of Au as 14.45 grams of NaAuCl solution having an Au concentration of 12.46%, and 0.3 grams of Cu as 0.8 grams of $CuCl_2$ dihydrate. Prior to diluting the Pd-Au-Cu solution to 328 cc, the solution is adjusted to a pH of about 6 with 7.17 grams of sodium bicarbonate. The Pd-Au-Cu impregnated bead is dried to about 1% moisture, then reduced in 1550 cc of boiling water containing 56 grams of sodium formate. The catalyst beads are held in contact with the hot formate solution for 30 minutes then washed and dried as shown for the above Example 7. The catalyst is spray impregnated with 31 grams of potassium acetate diluted to 350 cc with deionized water and dried overnight at 110° C.

EXAMPLE 10

Pretreated silica beads are prepared according to Example 4, except that the one liter, 76 grams, of KA-160 is pretreated with 24.3 grams of KOH and the amount of potassium silicate solution is 97.5 grams which is diluted with deionized water to 339 cc.

EXAMPLE 11

A Pd-Au catalyst is prepared by repeating Example 5, except that the catalyst is further spray impregnated with 30 grams of potassium acetate diluted with deionized water to 298 cc of total volume and again dried at 110° C. overnight.

EXAMPLE 12

Pretreated silica beads are prepared by impregnating one liter of KA-160 silica beads with 16.2 grams of potassium hydroxide and 127.2 grams of potassium silicate solution identified in Example 1 diluted with deionized water to 319 cc in total volume. The impregnation is in accordance with the procedure of Example 1. The impregnated beads are aged for 40 hours and then dried as described in Example 1. Following the procedure of Example 2, a Pd-Au-Cu catalyst is prepared by impregnating the pretreated silica beads of this example with 330 cc of an aqueous solution containing 4.1 grams of Pd, as 23.74 grams of $Na_2PdCl_4$ having a Pd concentration of solution 17.27% 1.8 grams Au, as 14.45 grams of $NaAuCl_4$ solution having an Au concentration of 12.46% and 0.15 gram of Cu, as 0.8 gram of $CuCl_2$ dihydrate. This catalyst is also further impregnated in accordance with the procedure of Example 3 with potassium acetate at a level of 22 grams per liter of catalyst and dried overnight at 110° C.

EXAMPLE 13

The procedure for Example 12 is repeated, except 1.47 grams of copper chloride dihydrate is used place of 0.15 grams of copper chloride dihydrate.

EXAMPLE 14

The procedure of Example 12 is repeated, except that one liter of KA-160 silica beads is used and the silica is pretreated with a mixture of 105.4 grams of a sodium silicate commercially available as N-BRAND from PQ Corp. containing 28.6% by weight of silica and 10.28 grams of NaOH.

EXAMPLE 15

A Pd-Au-Cu catalyst is prepared by impregnating one liter, 575 grams, of the pretreated beads prepared in Example 14 by uniformly spraying the pretreated beads while they are tumbled and mixed in a rotating coater with the following solution: 4.1 grams Pd (as 23.74 grams of palladium tetrachloride solution having a Pd concentration of 17.27% by weight), 1.8 grams of gold (as 9.83 grams of sodium tetrachloride solution having a gold concentration of 18.31% by weight) and 0.3 grams of copper (as 0.804 grams of copper chloride dehydrate) diluted with ionized water to a volume of 340 cc.

The Pd-Au-Cu impregnated beads are aged for 40 hours in a closed vessel and then reduced in 450 cc of deionized water combined with 17 grams of 35% hydrazine solution. After contact with the hydrazine solution for about two hours, the beads were washed with flowing deionized water until the wash water conductivity was below 100 micro mhos. The reduced catalyst is washed and dried as described for Example 2.

The catalyst is further spray impregnated in a rotating coater with 22 grams of potassium acetate which was diluted to 335 cc of total volume and then dried overnight at 110° C.

EXAMPLE 16

In this example, the silica beads used are commercially available as AF-125 from Kalie-Chemie Company which have a nominal diameter of 3–5mm, surface area of 300 square meters per gram and water adsorption porosity of 0.86 cc per gram. The procedure of Example 1 is repeated except that two liters, 954 grams, of AF-125 are impregnated with 837 cc of an aqueous solution containing 209.5 grams of KASIL No. 6 potassium silicate solution and 32.4 grams of potassium hydroxide.

EXAMPLE 17

The procedure of Example 2 is repeated except that one liter of the pretreated beads prepared in Example 16 are uniformly spray impregnated with 388 cc of an aqueous solution containing 24.33 grams of $Na_2PdCl_4$ solution (17.27% Pd containing 4.2 grams of Pd), 14.81 grams of $NaAuCl_4$ solution (12.46% Au containing 1.84 grams of Au) and 0.83 grams of $CuCl_2\text{-}2H_2O$ (containing 0.307 grams of copper).

EXAMPLE 18

The procedure of Example 3 is repeated except that catalyst of Example 17 is further impregnated with 297 cc of an aqueous solution containing 21.25 grams of potassium acetate. This results in a loading of 25 grams of potassium acetate per liter of catalyst.

EXAMPLE 19

In this example, $\frac{3}{16}^{th}$ inch $\times \frac{3}{16}^{th}$ inch silica tablets are used as the support. These tablets have a nominal water adsorption pore volume of 0.63 cc per gram, a bulk density of 650 grams per liter and a surface area of 195 square meters per gram. The procedure of Example 1 is repeated, except that 975 grams, 1.5 liters, of the above tablets are impregnated with 613 cc of an aqueous solution containing 24.3 grams of potassium hydroxide and 172 grams of KASIL No. 6 potassium silicate solution.

EXAMPLE 20

The procedure of Example 2 is repeated, except that one liter, 651.5 grams, of pretreated tablets prepared in Example 19 are impregnated with 345 cc of an aqueous solution containing 24.57 grams of $Na_2PdCl_4$ solution (17.27% Pd, containing 4.24 grams of Pd), 14.95 grams of $NaAuCl_4$ solution (12.46% Au, containing 1.86 grams of Au) and 0.83 grams of $CuCl_2\text{-}2H_2O$ (containing 0.31 grams of copper) and in accordance with Example 3 impregnating 850 cc, 552.5 grams, of the reduced, washed and dried catalyst with 285 cc of an aqueous solution containing 21.25 grams of potassium acetate. This results in a loading of 25 grams of potassium acetate per liter of catalyst. The catalyst is then dried overnight at 110° C.

EXAMPLE 21

Pretreated silica beads are prepared by impregnating 12 liters, 6,960 grams, of KA-160 silica beads, which have been dried overnight at 115° C., with 4,275 cc of an aqueous solution containing 191.3 grams of potassium hydroxide and 1449.2 grams of KASIL No. 6 potassium silicate solution described in Example 1. This solution is sprayed on the beads while they are being tumbled in a rotating coater over a period of about 35 minutes. This corresponds to pretreatment with 15.9 grams of KOH and 120.8 grams of potassium silicate solution per liter of support.

The pretreated beads are then aged in a closed container at room temperature for 40 hours and returned to the coater and dried with flowing warm air of 50°–70° C. while tumbling until the residual moisture content is 0.5%.

The pretreated beads are then uniformly spray impregnated in a rotating coater with 4143 cc of an aqueous solution containing 50.43 grams of palladium as 292 grams of $Na_2PdCl_4$ solution (17.27% Pd), 22.14 grams of gold as 177.69 grams of $NaAuCl_4$ solution (12.46% Au) and 9.9 grams of $CuCl_2\text{-}2H_2O$ (containing 3.69 grams of copper). These Pd-Au-Cu impregnated beads are aged, then reduced with 71.4 grams of hydrazine dissolved in 6 liters of deionized water, then washed and dried in the same fashion as in Example 2.

EXAMPLE 22

A catalyst is prepared by impregnating 10 liters, 5930 grams, of the catalyst prepared in Example 21 with 3498 cc of an aqueous solution containing 220 grams of potassium acetate in accordance with the procedure of Example 3. This corresponds to a potassium acetate loading of 22 grams per liter of catalyst. After impregnation, the catalyst is dried overnight at 110° C.

EXAMPLE 23

A catalyst is prepared from by impregnating 850 cc, 504 grams, of the catalyst prepared in Example 21 with 297 cc of an aqueous solution containing 29.75 grams of potassium acetate in accordance with the procedure of Example 3. This corresponds to a potassium acetate loading of 35 grams per liter of catalyst. After impregnation, the catalyst was dried overnight at 110° C.

EXAMPLE 24

A Pd-Au-Ni catalyst is prepared by uniformly spray impregnating 400 cc (268 grams) of pretreated beads prepared in Example 1 in a rotating coater with 140 cc of an aqueous solution containing 9.95 grams of sodium palladium tetrachloride solution (16.49% Pd), 3.26 grams of sodium gold tetrachloride solution (22.09% Au) and 0.486 grams of nickel chloride hexahydrate. This corresponds to metal loadings of 4.1 grams of palladium, 1.8 grams of gold and 0.3 grams of nickel per liter of catalyst.

The Pd-Au-Ni impregnated beads are aged overnight at room temperature, reduced in 250 cc of deionized water containing 6 grams of hydrazine for two hours, then washed with flowing deionized water until the wash water had a conductivity under 100 micro mhos and then dried at 110°–120° C. to a residual moisture content of less than 2%.

This Pd-Au-Ni catalyst, now weighing 264 grams, is further spray impregnated in a rotary coater with 134.6 cc of an aqueous solution containing 12 grams of potassium acetate dissolved in deionized water. This corresponds to a potassium acetate loading of 30 grams per liter of catalyst. After impregnating with potassium acetate solution, the catalyst is dried overnight in a forced air oven held at 110° C. to a moisture content of less than 2%.

EXAMPLE 25

The procedure of Example 2 is repeated except the Pd-Au-Cu impregnated beads are aged overnight instead for 44 hours. This catalyst is uniformly spray impregnated in a rotary coater with potassium acetate to a level of 30 grams per liter by impregnating it with 130 cc of an aqueous solution containing 12 grams of potassium acetate then drying at 110° C. overnight.

EXAMPLE 26

A catalyst is prepared by uniformly spray impregnating 850 cc, 504 grams, of the catalyst prepared in Example 22 in a rotary coater with 297 cc of an aqueous solution containing 12.75 grams of potassium acetate. This corresponds to a potassium acetate loading of 15 grams per liter of catalyst. After impregnation, the catalyst is dried overnight at 110° C.

EXAMPLE 27

A catalyst is prepared by uniformly spray impregnating 850 cc, 504 grams, of the catalyst prepared in Example 22 with 297 cc of an aqueous solution containing 25.93 grams of potassium acetate. This corresponds to a potassium acetate loading of 30.5 grams per liter of catalyst. After impregnation, the catalyst is dried overnight at 110° C.

EXAMPLE 28

A Pd-Au catalyst is prepared by uniformly spray impregnating one liter, 575 grams, of KA-160, in a rotary coater with 339 cc of an aqueous solution containing 16.2 grams of potassium hydroxide. The KOH-impregnated beads are aged in a covered container at room temperature for about 40 hours and then dried at about 70° C. on a vibrating lab drier to a moisture level of 0.5%. After drying, the beads are placed in a two liter titanium rotating lab coater and uniformly spray impregnated with 300 cc of an aqueous solution containing 4.1 grams of Pd, 23.74 grams of sodium palladium tetrachloride solution with a Pd concentration of 17.27% by weight and 1.8 grams of gold, as 9.83 grams of sodium gold tetrachloride solution with an Au concentration of 18.31% by weight.

The Pd-Au impregnated beads are aged at room temperature for about 40 hours, reduced in 500 cc of deionized water containing 5.9 grams of hydrazine, washed and dried in accordance with the procedure of Example 7, and then spray impregnated with 30 grams of potassium acetate dissolved in 306 cc of deionized water and dried overnight at 110° C.

EXAMPLE 29

Pretreated silica beads are prepared by impregnating one liter (575 grams) of KA-160 beads with 300 cc of a solution containing 138.5 grams of the potassium silicate solution identified in Example 1 by uniformly spraying this solution on the beads while they are tumbled and mixed in a rotating coater. The silicate pretreated beads are aged and dried.

These pretreated beads are then impregnated with 300 cc of an aqueous solution containing 4.1 grams of Pd (as 23.74 grams of sodium palladium tetrachloride solution having a Pd concentration of 17.27% by weight) and 1.8 grams of gold (as 9.83 grams of sodium gold tetrachloride solution having an Au concentration of 18.31% by weight) by uniformly spraying the Pd-Au solution on the pretreated beads while they are tumbled and mixed in a rotating coater.

The Pd-Au impregnated beads are reduced with 5.9 grams hydrazine dissolved in 500 cc of deionized water, then washed and dried in the same fashion as Example 2. One liter of this catalyst is uniformly spray impregnated in a rotary coater with 30 grams of potassium acetate diluted with deionized water to a volume of 315 cc. The catalyst is then dried overnight at 110° C.

EXAMPLE 30

The procedure of Example 29 is repeated except 16.9 grams of potassium hydroxide is used in place of 16.2 grams of KOH in preparing the pretreated silica beads.

EXAMPLE 31

A Pd-Au catalyst is prepared by impregnating 1.2 liters (576 grams) of the AF-125 silica beads described in Example 16 with 490 cc of a solution containing 27.57 grams of Na$_2$PdCl$_4$ solution (17.63% Pd, containing 4.86 grams of Pd), and 10.08 grams of NaAuCl$_4$ solution (22.03% Au, containing 2.22 grams of Au). These amounts correspond to metal loadings of 4.05 grams of Pd per liter of support and 1.85 grams of Au per liter of support. The Pd-Au impregnated beads are aged while tumbling in the rotating coater for about 10 minutes. A 200 cc portion of these Pd-Au impregnated beads are then soaked in 100 cc of 5.2% aqueous sodium meta silicate solution for 16 hours. The beads are then removed from the silicate solution and reduced in a solution consisting of 85 cc of deionized water combined with 15 cc of 35% aqueous hydrazine for 2 hours, then washed and dried as described in Example 2. After drying, 200 cc of this catalyst is further uniformly spray impregnated in a rotary coater with 6.2 grams of potassium acetate and then dried overnight at 110° C.

EXAMPLE 32

Pretreated silica beads are prepared by impregnating 18 liters, 10242 grams, of KA-160 placed in a 40 liter plastic lab coater and sprayed while tumbling in the coater with 3,000 cc of an aqueous solution containing 224.2 grams of sodium hydroxide. The beads are tumbled in the coater for about 15 minutes after the NaOH solution is sprayed on to insure uniform mixing. The beads are then impregnated with palladium and gold by spraying them with 3040 cc of an aqueous solution containing 79.69 grams of Pd as 461.5 grams of sodium palladium tetrachloride (17.27% Pd) and 35.48 grams of gold as 183.7 grams of sodium gold tetrachloride (19.31% Au). These amounts correspond to 4.42 grams of Pd and 1.97 grams of Au per liter of catalyst.

These Pd-Au impregnated beads are allowed to age for 50 hours and then reduced in 9 liters of deionized water combined with 300 cc of 35% aqueous hydrazine solution. After remaining in overnight contact with the hydrazine solution, the beads are washed with deionized water until the wash water had a conductivity of less than 5 micro mhos. The beads are then dried overnight at 110° C. before testing. The dried catalyst has a moisture content of 20.1%, a bulk density of 662 grams per liter and a water adsorption pore volume of 0.31 cc per gram.

EXAMPLE 33

A catalyst is prepared by impregnating 12 liters, 7944 grams, of the catalyst prepared in Example E with 2480 cc of an aqueous solution containing 360 grams of potassium acetate. This amount corresponds to a potassium acetate loading of 30 grams per liter of catalyst. After impregnation, the catalyst was dried overnight at 110° C.

CATALYST EVALUATION

The results shown in Table I were conducted in a fixed bed test reactor operating as a vapor phase reactor. The reactor is a ⅜″ outside diameter 316 stainless steel tube with a catalyst bed capacity of approximately 55 cc. Typical operating conditions are: Temperature=100°-150° C., Pressure=30-120 psig. GHSV 250-1000, Gas composition 76% $C_2H_4$, 18% $CH_3COOH$, 6% $O_2$. Inlet gas flows are set through use of mass flowmeters and control valves. Outlet gas compositions are measured through use of a gas-liquid chromatograph. Temperatures are monitored through thermocouples placed in a fluidized and heated sand bath surrounding the reactor and a thermocouple placed in the catalyst bed. Gas preheaters are used to insure that all components are in the vapor phase before they enter the reactor. Reaction conditions and run sequencing are controlled through use of data acquisition and control computers.

Performance data are calculated through the use of inlet flows and outlet gas analyses. The performance data reported are space time yield in grams vinyl acetate/liter catalyst hour and ethylene selectivity in grams vinyl acetate produced/grams ethylene consumed.

A catalyst evaluation sequence consists of several steps. The reaction is started by flowing ethylene and acetic acid over the catalyst at 140° C. and 35 psig, then slowly increasing the oxygen flow until the desired 6% concentration is reached. The catalyst is held at constant conditions of composition, flow, temperature, and pressure for a period of time (50 to 100 hours) to allow any initial performance changes to occur and allow the catalyst to reach a steady state of performance. The reaction temperature is then varied in 10° C. increments over a range from 100°-150° C. Several gas chromatographic analyses of the reactor effluent are taken at each temperature, typically 120°, 130°, and 140° C. Space time yield and selectivity results are generated from the chromatographic analysis and reactor feed data. The results obtained at each temperature are averaged and a selectivity and space time yield vs. temperature table is generated. When two catalysts are compared, the superior catalyst has greater activity at constant selectivity, and/or greater selectivity at constant activity. The results of the Examples identified in Table 1 are compared at space time yields (STY) at 95% ethylene selectivity and selectivities at 125 space time yield.

| PERFORMANCE EVALUATIONS SPACE TIME YIELDS (STY) & SELECTIVITIES | | |
|---|---|---|
| Example No. | STY @ 95% Sel. | Sel. @ 125 STY |
| 3 | 158.3 | 96.3 |
| 5 | 130.6 | 95.3 |
| 6 | 132.5 | 95.6 |
| 7 | 137.0 | 95.9 |
| 8 | 130.5 | 95.4 |
| 11 | 117.0 | 94.7 |
| 12 | 137.2 | 96.5 |
| 13 | 137.2 | 95.6 |
| 15 | 128.4 | 95.3 |
| 18 | 160.0 | 95.8 |
| 20 | 147.5 | 95.8 |
| 21 | 96.4 | 91.4 |
| 22 | 155.0 | 96.1 |
| 23 | 143.0 | 95.7 |
| 24 | 131.7 | 95.3 |
| 25 | 120.0 | 94.4 |
| 28 | 135.3 | 95.6 |
| 29 | 87.6 | 92.5 |
| 30 | 109.4 | 94.0 |
| 31 | 101.3 | 93.1 |
| 32 | <20 | |
| 33 | 125.0 | 95.0 |
| * | 91.7 | 93.0 |

*Comparative example - a Pd-Au reference catalyst supported on KA-160 (no pretreatment of support with silicate and base and only sodium salts used in Pd-Au metal deposition) having 3.89 grams Pd/liter of catalyst, 1.79 grams of Au/liter of catalyst and a potassium acetate loading of 30 grams per liter of catalyst.
Cannot determine The catalysts and processes of this invention provide improved unsaturated ester yield and selectivity of olefin to unsaturated ester and in particular the catalysts of this invention can maintain their activity in the absence of activators such as potassium acetate during the process of preparing unsaturated esters.

What is claimed:

1. A process for preparing ethylenically unsaturated esters comprising reacting in the vapor phase at least one olefinic compound with at least one carboxylic acid and molecular oxygen in the presence of an effective amount of a catalyst composition comprising (i) one or more palladium group metals and/or compounds thereof, (ii) gold and/or compounds thereof, and (iii) one or more promoters selected from the group consisting of copper, nickel, cobalt, iron, manganese, lead, silver and compounds thereof; wherein the gram-atom ratio of metal in the promoter to palladium group metal is up to about 0.4.

2. A process according to claim 1 wherein the gram-atom ratio of the metal in the promoter to palladium group metal is from about 0.04 up to about 0.2.

3. A process according to claim 1 wherein said promoter is copper and/or compounds thereof, nickel and/or compounds thereof and mixtures thereof.

4. A process according to claim 1 wherein the gram-atom ratio of gold to palladium group metal is from about 0.1 up to about 0.5.

5. A process according to claim 1 wherein said catalyst composition is deposited on a carrier support.

6. A process according to claim 5 wherein the support is silica.

7. A process according to claim 6 wherein, prior to deposition of said catalyst on said support, the support is treated with one or more alkali metal bases and one or more alkali metal silicates.

8. A process according to claim 1 wherein said support is treated by (a) wetting the support with a mixture of one or more alkali metal hydroxides and one or more alkali metal silicates, (b) aging the wetted support and (c) then drying the aged and wetted support.

9. A process for preparing ethylenically unsaturated esters comprising reacting in the vapor phase at least one olefinic compound with at least one carboxylic acid and molecular oxygen in the presence of an effective amount of a catalyst composition comprising (i) one or more palladium group metals and/or compounds thereof; (ii) gold and/or compounds thereof; and (iii) one or more promoters selected from the group consisting of copper, nickel, cobalt, iron, manganese, lead, silver and compounds thereof; wherein said catalyst is deposited on a support material and said support material is treated with one or more alkali metal bases and one or more alkali metal silicates prior to said deposition.

10. A process according to claim 9 wherein said palladium group metal is palladium, said promoter is copper and/or compounds thereof, nickel and/or compounds thereof or mixtures thereof and the gram-atom ratio of metal in the promoter to palladium is from about 0.04 up to about 0.2.

11. A process according to claim 10 wherein the gram-atom ratio of gold to palladium is about 0.1 up to about 0.5.

12. A process according to claim 9 wherein said support is treated by (a) wetting the support with a mixture of one or more alkali metal hydroxides and one or more alkali metal silicates, (b) aging the wetted support and (c) then drying the aged and wetted support.

13. A process according to claim 10 wherein said support is silica.

14. A process for preparing ethylenically unsaturated esters comprising reacting in the vapor phase at least one olefinic compound with at least one carboxylic acid and molecular oxygen in the presence of an effective amount of a catalyst composition comprising (i) one or more palladium group metals and/or compounds thereof; and (ii) gold and/or compounds thereof; wherein said catalyst is deposited on a support material and said support material is treated with one or more alkali metal bases and one or more alkali metal silicates prior to said deposition.

15. A process according to claim 14 wherein the gram-atom ratio of gold to palladium is about 0.1 up to about 0.5.

16. A process according to claim 14 wherein said support is treated by (a).wetting the support with a mixture of one or more alkali metal hydroxides and one or more alkali metal silicates, (b) aging the wetted support and (c) then drying the aged and wetted support.

17. A process according to claim 14 wherein said support is silica.

* * * * *